United States Patent
Sengun

(10) Patent No.: US 8,251,974 B2
(45) Date of Patent: Aug. 28, 2012

(54) VAPOR ASSISTED FLUID CUTTING DEVICE AND METHOD

(75) Inventor: Mehmet Z. Sengun, Braintree, MA (US)

(73) Assignee: DePuy Mitek, Inc., Raynham, MA (US)

( * ) Notice: Subject to any disclaimer, the term of this patent is extended or adjusted under 35 U.S.C. 154(b) by 0 days.

(21) Appl. No.: 12/951,523

(22) Filed: Nov. 22, 2010

(65) Prior Publication Data

US 2011/0125173 A1    May 26, 2011

Related U.S. Application Data

(62) Division of application No. 11/306,751, filed on Jan. 10, 2006, now Pat. No. 7,867,187.

(51) Int. Cl.
*A61M 31/00* (2006.01)
*A61B 17/32* (2006.01)

(52) U.S. Cl. ........................... 604/500; 606/167

(58) Field of Classification Search ............... 604/19
See application file for complete search history.

(56) References Cited

U.S. PATENT DOCUMENTS

| | | | |
|---|---|---|---|
| 5,632,739 A * | 5/1997 | Anderson et al. | 606/2 |
| 5,891,134 A * | 4/1999 | Goble et al. | 606/27 |
| 6,352,535 B1 | 3/2002 | Lewis et al. | |
| 6,582,040 B2 | 6/2003 | Coven et al. | |
| 7,867,187 B2 | 1/2011 | Sengun | |
| 2002/0045911 A1* | 4/2002 | Fletcher et al. | 606/167 |
| 2002/0186967 A1 | 12/2002 | Ramanan et al. | |
| 2004/0199226 A1 | 10/2004 | Shadduck | |
| 2008/0243157 A1 | 10/2008 | Klein et al. | |

OTHER PUBLICATIONS

Summers, David A., "Waterjetting Technology," First Edition, Chapman & Hall, 1995, Ch. 10, pp. 667-781.
"ExoJet Fluid-Jet Resection System: The cool choice for tissue sculpting and bone removal"; Mitek Worldwide, Dec. 2002, 4 pages.

* cited by examiner

*Primary Examiner* — Christopher D Koharski
*Assistant Examiner* — Jason Flick

(57) ABSTRACT

Various methods and devices are provided for cutting tissue using a high pressure fluid jet. In one exemplary embodiment, a high pressure fluid jet delivery device is provided having a nozzle adapted to direct fluid to a tissue site. A heating element is disposed on the nozzle and is adapted to heat fluid surrounding a high pressure fluid jet flowing from the nozzle to form at least one vapor bubble. The vapor bubble can reduce the interaction between the high pressure fluid jet and the fluid surrounding the high pressure fluid jet.

6 Claims, 4 Drawing Sheets

VAPOR ASSISTED FLUID CUTTING DEVICE AND METHOD

CROSS-REFERENCE TO RELATED APPLICATIONS

This application is a divisional of U.S. patent application Ser. No. 11/306,751 filed on Jan. 10, 2006 and entitled "Vapor Assisted Fluid Cutting Device and Method," which is hereby incorporated by reference in its entirety.

BACKGROUND OF THE INVENTION

High pressure fluid jet systems for cutting tissue and removing bone are known in the art. Fluid jet cutters focus pressurized fluid to impact desired target tissue and thereby emulsify the tissue. The tissue can then be suctioned or otherwise removed from the surgical site. While current fluid jet cutters are effective, when the fluid jet system is submerged in a liquid environment, such as water, the fluid jet interacts with the surrounding liquid, resulting in a reduction of the strength or cutting power of the fluid jet.

Various techniques have been used to address this problem. One of the earliest attempts to improve the performance of fluid jet cutters was to use a sheath around the jet such that the jet could travel through air in a fluid environment. The air allows the fluid to flow at a faster rate and at a greater distance, improving the efficiency of the device when used in a liquid environment. While the air shroud was shown to improve efficiency, there are additional disadvantages that come with this improved efficiency, including visualization and environmental disturbances when the air interacts with the surrounding fluid.

Accordingly, there is a need for improved devices and methods for cutting tissue using a high pressure fluid jet, preferably while minimizing the interaction between the fluid jet and the surrounding liquid environment.

BRIEF SUMMARY OF THE INVENTION

The present invention generally provides devices and methods for cutting tissue using a high pressure fluid jet delivery device. While this can be achieved using a variety of techniques and devices, in one embodiment, the device can include a nozzle adapted to direct fluid to a tissue site, and a heating element disposed on the nozzle and adapted to heat fluid surrounding a high pressure fluid jet flowing from the nozzle to form at least one vapor bubble. The vapor bubble(s) can reduce the interaction between the high pressure fluid jet and the fluid surrounding the high pressure fluid jet. In one exemplary embodiment, the nozzle can be formed on a distal end of an elongate shaft, and a proximal end of the elongate shaft can include a handle formed thereon and adapted to couple to a high pressure fluid pump. The device can also include first and second conductive wires coupled to the heating element for delivering energy thereto.

The heating element can have a variety of configurations, and it can be disposed at various locations around, on, or within the nozzle. In one exemplary embodiment, the heating element is disposed around a distal end surface of the nozzle, and it has an annular ring-shaped configuration. The heating element can include, for example, a conductive member that is adapted to heat the fluid surrounding the high pressure fluid jet and optionally, various other members to facilitate heating. For example, the heating element can include a thermoisolating member disposed between a distal end surface of the nozzle and the conductive member, and/or a heat accumulating layer disposed between a distal end surface of the nozzle and the conductive member. The heating element can also include a protective coating disposed around the heating element.

Also disclosed herein are methods for cutting tissue using a high pressure fluid delivery device. In one embodiment, the method can include delivering a high pressure fluid jet through a liquid environment to cut tissue at a target site, and heating the liquid environment surrounding the high pressure fluid jet to form at least one vapor bubble adjacent to the fluid jet. The vapor bubble can reduce the friction between the fluid jet and the liquid environment. In certain exemplary embodiments, the high pressure fluid jet can be delivered through a nozzle which can include a heating element formed thereon. Energy delivered to the heating element heats the liquid environment. The energy delivered to the heating element can be pulsed to form multiple vapor bubbles, or it can be constant to form a substantially constant vapor bubble. In one exemplary embodiment, the high pressure fluid jet can be delivered at a pressure in the range of about 500 psi to 15000 psi.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for cutting tissue using a high pressure fluid jet delivery system. In particular, the methods and devices are configured to heat fluid surrounding a high pressure fluid jet in order to form one or more vapor bubbles around the fluid jet, thereby reducing the friction generated between the fluid environment and the high pressure fluid jet.

Figure 1:
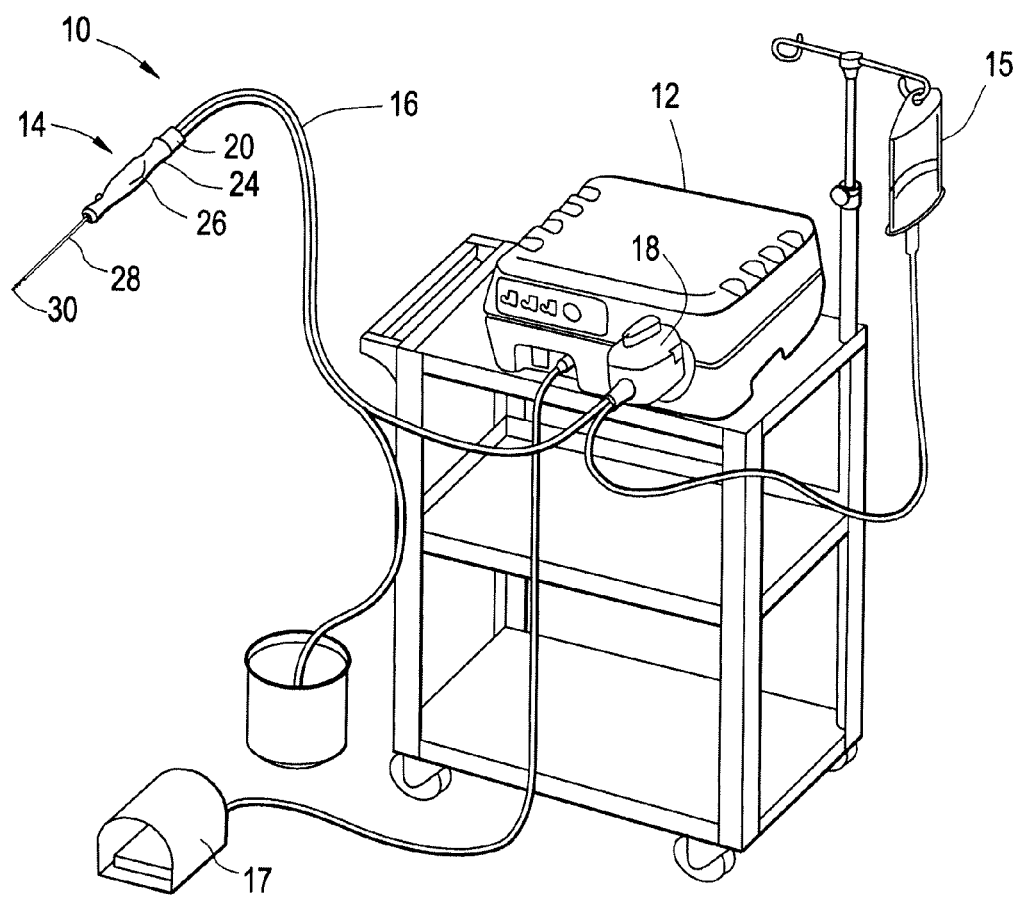
FIG. 1 is an illustration of a high pressure fluid jet delivery system having a high pressure fluid jet delivery device, and a pump for pumping fluid through the device.

While various high pressure fluid jet delivery systems can be used, FIG. 1 illustrates one exemplary embodiment of a high pressure fluid jet delivery system 10 for cutting tissue using a high pressure fluid jet. As shown, high pressure fluid jet delivery system 10 includes a fluid jet cutting device 14 for delivering the high pressure fluid jet to a tissue to be cut. The fluid jet cutting device 14 can be coupled to a pump 12 which delivers fluid to the fluid jet cutting device 14 through a fluid delivery tube 16. Fluid delivery from the pump 12 can be actuated using a variety of techniques, such as a foot pedal 17. The fluid can be stored in the pump 12, or the pump 12 can couple to an external fluid source 15, as shown. The fluid delivery tube 16 that extends between the pump 12 and the fluid jet cutting device 14 can have a variety of configurations, and it can be rigid or flexible. As shown in FIG. 1, the fluid jet delivery tube 16 includes a distal end which is coupled to the fluid jet cutting device 14 by a distal connector 20, and a proximal end which is coupled to the pump 12 by a proximal connector 18. In another embodiment, the fluid jet delivery tube 16 can be coiled and flexible to allow free movement of the fluid jet cutting device 14.

Figure 2:
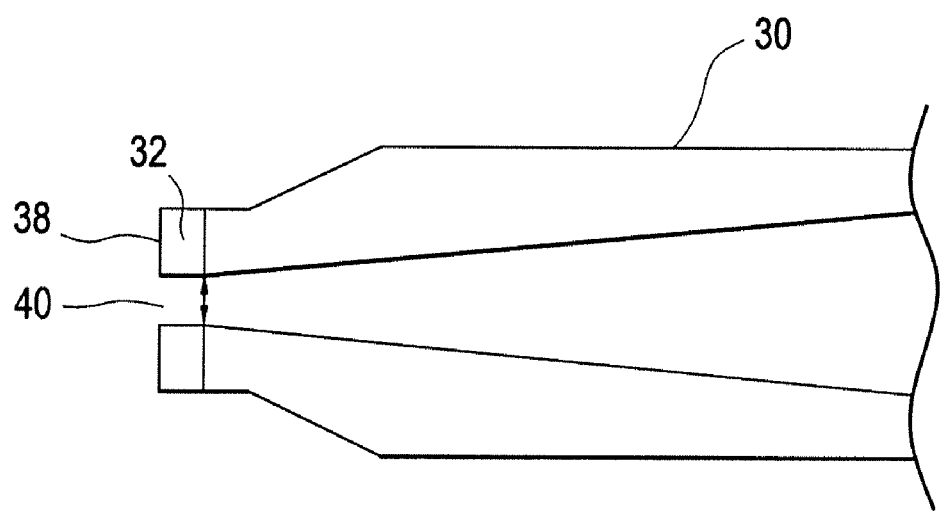
FIG. 2 is a cross-sectional view of a nozzle of the high pressure fluid jet delivery device shown in FIG. 1, showing a heating element disposed on a distal end of the nozzle.
Figure 3A:
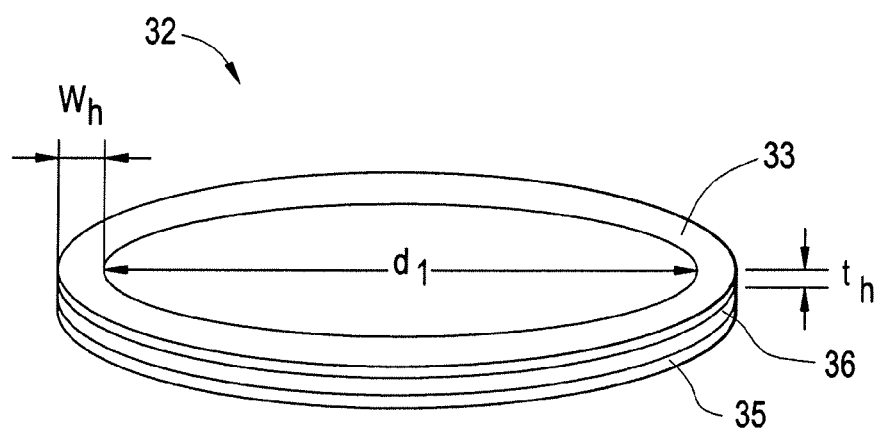
FIG. 3A is a perspective view of the heating element shown in FIG. 2, having a heat accumulating layer, a thermoisolating member, and a conductive member.
Figure 3B:
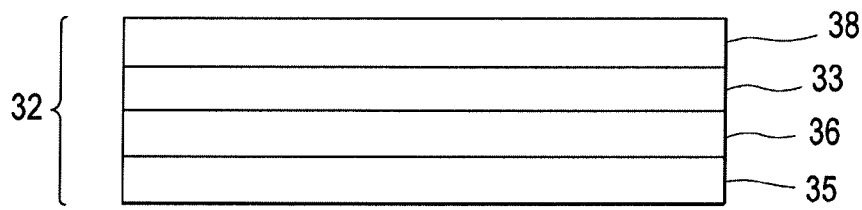
FIG. 3B is a cross-sectional view of the heating element shown in FIG. 3A.

The fluid jet cutting device 14 can also have a variety of configurations. As shown in FIG. 1, it includes a handle 24 adapted to allow a user to grip the fluid jet cutting device 14 and a shaft 28 extending from the handle 24. A nozzle 30 is disposed on the distal end of the shaft 28 and is adapted to direct the high pressure fluid jet toward tissue to be cut. A heating element 32, shown in FIGS. 2-3B, is disposed on the distal end of the nozzle 30 and is adapted to heat the fluid in the liquid environment surrounding the high pressure fluid jet to produce vapor bubbles. In use, the fluid jet cutting device 14 is coupled to the pump 12 of the high pressure fluid delivery system 10 and fluid is delivered from the pump 12 through the fluid delivery tube 16 to the fluid jet cutting device 14. The fluid travels through the shaft 28 to the nozzle 30. The nozzle 30 forms the high pressure fluid jet and directs it toward a tissue to be to cut. When energy is delivered to the heating element 32 from an energy source (not shown), vapor bubbles are formed to surround the high pressure fluid jet to decrease its interaction with the surrounding liquid environment when it is submerged in liquid.

The handle 24 can have any shape or size to facilitate gripping of the device. The handle 24 can also include various features, such as an actuator 26 for controlling the delivery of energy to the heating element 32. By way of non-limiting example, the actuator 26 can be in the form of a button, a switch, a knob, or any other configuration to allow for the control of energy from the energy source. In lieu of an actuator disposed on the handle 24, one skilled in the art will appreciate that the actuator 26 can be located elsewhere, including on a foot pedal. The energy source can be provided from a variety of sources, such as from an outlet or an internal or external battery source. For example, the energy source, can be supplied through the pump 12 via a power cord which connects to a power outlet.

The shaft 28 that extends from the distal end of the handle 24 can be flexible or rigid depending on its intended use. The shaft 28 can include an inner lumen (not shown) for receiving fluid flow from the fluid delivery tube 16 and for directing the fluid to the nozzle 30. The nozzle 30 is formed on or is coupled to the distal end of the shaft 28, and it forms the high pressure fluid jet and directs the high pressure fluid jet toward a target site, for example, a tissue to be cut, through a distal opening 40 (shown in FIG. 2) in the nozzle 30. A person skilled in the art will appreciate that virtually any nozzle can be used, and that the fluid jet cutting device 14 can have a variety of other configurations.

As previously indicated, the device can also include a heating element 32 formed on or coupled to the nozzle 30 for heating the liquid environment surrounding the high pressure fluid jet flowing from the nozzle 30. The heating element 32 can have a variety of configurations, shapes, and sizes, and it can be positioned at various locations on the nozzle 30. In the illustrated embodiment, as shown in FIG. 2, the heating element 32 is disposed on a distal end surface of the nozzle 30 and it surrounds the opening 40 from which the high pressure fluid jet flows. In particular, the illustrated heating element 32 is in the form of an annular ring-shaped member, which is shown in more detail in FIGS. 2-3. The annular ring-shaped heating element 32 can vary in size depending on the size of the opening 40 in the nozzle 30, but it preferably has an inner diameter $d_i$ that is equal to or greater than a diameter $d_o$ of the opening in the nozzle 30 such that it does not block the opening 40. The surface area of the heating element 32 can also vary, but it preferably has a surface area greater than the surface area of the opening 40. The height or thickness $t_h$ and the width $w_h$ of the heating element 32 can also vary depending on the properties of the material used to form the heating element 32, and the amount of heat intended to be generated by the heating element 32. Preferably, the heating element 32 has dimensions that are effective to generate a vapor bubble that substantially surrounds a fluid jet flowing from the nozzle 30.

The materials used to from the heating element 32 can also vary. In an exemplary embodiment, as shown, the heating element 32 includes a conductive member 33 that is configured to heat up when energy is delivered thereto. Energy delivery to the conductive member 33 can be achieved using, for example, conductive wires or leads extending along the length of the shaft 28 of the fluid jet cutting device 14. By way of non-limiting example, the conductive member 33 can be formed from a variety of conductive materials, such as nickel-chromium (NiCr), titanium nitride (TiN), or tantalum-aluminum (TaAl), in the shape of a conductive wire, sheet, substrate, or surface deposition.

The heating element 32 can also include other components to protect the heating element 32, isolate it from the nozzle 30, and/or facilitate rapid cooling of the heating element 32. For example, as shown in FIGS. 3A-3B, the heating element 32 includes a thermoisolating member 36 disposed between the distal end surface of the nozzle 30 and the conductive member 33. The thermoisolating member 36 is configured to separate the conductive member 33 from the nozzle 30 to prevent the nozzle 30 from being heated. The thermoisolating member 36 can have a variety of configurations, for example, the thermoisolating member 36 can be in the form of a surface coating, or it can be in the form of a ring-shaped member, as shown in FIG. 3. A person skilled in the art will appreciate that the thermoisolating member 36 can have any configuration or shape that is capable of thermally isolating the conductive member 33 from the distal end surface of the nozzle 30. The thermoisolating member 36 can also be formed from a variety of materials. Exemplary materials include materials having a high heat resistance, such as plastics, ceramics, glass, and silicon dioxide ($SiO_2$). A person skilled in the art will appreciate that a thermoisolating member is not needed, and that in other embodiments, the nozzle 30 itself can be formed from a thermoisolating or heat resistance material to prevent the nozzle 30 from heating.

The heating element 32 can also or alternatively include a heat accumulating layer 35 disposed between the conductive member 33 and the nozzle 30 adapted to act as a heat sink to allow the conductive member 33 to cool quickly. This is advantageous as it stops the creation of vapor bubbles when energy delivery to the heating element 32 is terminated and quickly cools the conductive member 33 to ambient conditions. The heat accumulating layer 35 can have a variety of configurations or shapes that allow the heat accumulating layer 35 to accumulate heat from the conductive member 33 by drawing heat from the conductive member 33 when energy delivery to the conductive member 33 is terminated. The heat accumulating layer 35 can also be formed from a variety of materials. Exemplary materials include copper, aluminum, zinc, and silicon (Si).

The heating element 32 can also optionally include a protective coating 38 disposed on the conductive member 33 and adapted to prevent vapor bubbles from attacking the surface of the conductive member 33. The protective coating 38 can be a surface coating that is sprayed on or otherwise disposed on the conductive member 33, or it can be a housing or other member that is disposed over the conductive member 33. A person skilled in the art will appreciate that the protective coating 38 can have any configuration or construction that insulates or protects the heating element 32 from the surrounding liquid environment and the vapor bubbles that are formed. The protective coating 38 can also be formed from a variety of materials, including, by way of non-limiting example, tantalum.

A person skilled in the art will appreciate that the heating element 32 can include any or none of the heat accumulating layer 35, the thermoisolating member 36, and the protective coating 38.

In use, energy is delivered to the heating element 32 to create vapor bubbles in the liquid environment surrounding the high pressure fluid jet. The energy source can be pulsed to create a multiple discrete vapor bubbles in the liquid environment, resulting in a chain of bubbles surrounding the high pressure fluid jet. The pulsed energy can vary in pulse shape and/or frequency depending on the number and size of vapor bubbles desired. Alternatively, the energy source can be delivered to the heating element 32 at a constant rate, creating an elongated vapor bubble surrounding the high pressure fluid jet. A person skilled in the art will appreciate that vapor bubbles can also be formed by merely warming the liquid (without boiling it at the heater surface) to facilitate cavitation of the surrounding fluid caused by the high pressure fluid jet.

Figure 4:
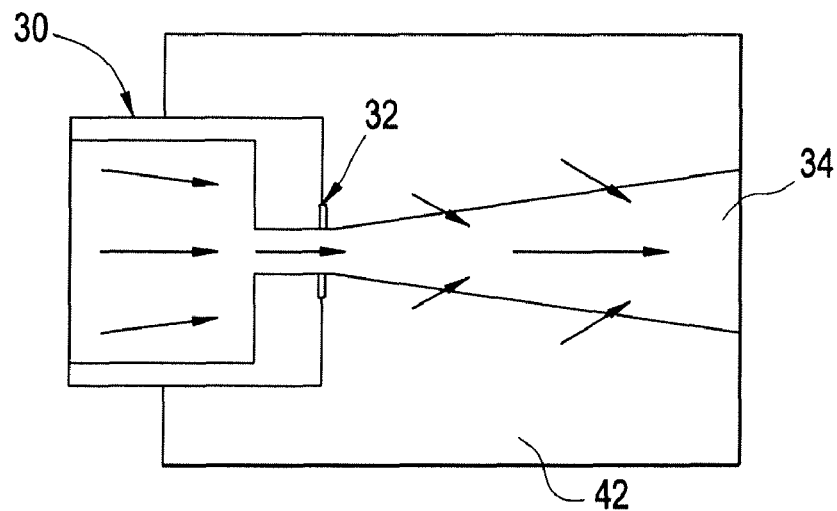
FIG. 4 is a cross-sectional view of the nozzle of FIG. 2 disposed within a liquid environment when energy is not being delivered to the heating element.
Figure 5:
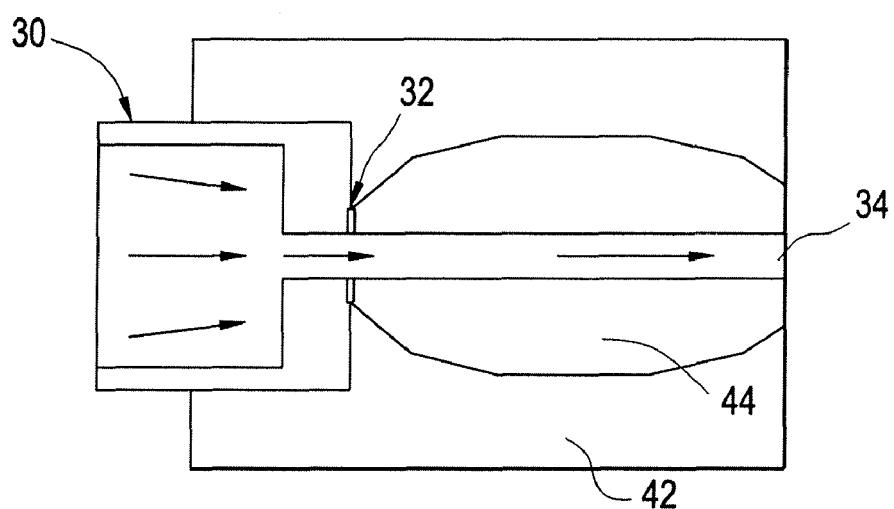
FIG. 5 is a cross-sectional view of the nozzle of FIG. 2 disposed within a liquid environment when energy is being delivered to the heating element, showing a vapor bubble formed around a fluid jet flowing from the nozzle.

FIG. 4 shows a high pressure fluid jet 34 within a liquid environment 42 when energy is not being delivered to a heating element 32. As soon as the high pressure fluid jet 34 leaves the opening in the nozzle 30, the high pressure fluid jet 34 interacts with the surrounding liquid environment 42, causing a hydrodynamic drag. This causes the high pressure fluid jet 34 to slow down, dissipate its power, and spread its energy distribution, resulting in a weakening of the high pressure fluid jet 34 and a decreased tissue cutting efficiency. When the heating element 32 is turned on, as shown in FIG. 5, a vapor bubble 44 is formed to shield the high pressure fluid jet 34 from the surrounding liquid environment 42, decreasing the interaction between the two liquids.

As the vapor bubbles move away from the heating element 32, they will thermally interact with the liquid environment. This causes the temperature of the vapor bubbles to decrease, resulting in the shrinking and eventual collapse of the vapor bubbles. Once the vapor bubbles are dissipated, they leave no traces behind, thus leaving a clear field of vision in the liquid environment that does not obscure the view of the tissue that is being cut with the high pressure fluid jet 34.

The high pressure fluid jet delivery device can be used in a variety of surgical procedures, but in one exemplary embodiment the high pressure fluid jet delivery device is used for sculpting and/or cutting tissue. In particular, the fluid jet delivery device can be introduced into a surgical site, and the high pressure fluid jet can be activated and directed toward a tissue and/or bone surface to thereby sculpt and/or cut the tissue and/or bone. Energy can be delivered to a heating element on a nozzle of the high pressure fluid jet delivery device to promote the formation of vapor bubbles in the liquid environment surrounding the high pressure fluid jet, thereby reducing friction between the high pressure fluid jet and the surrounding environment to allow the high pressure fluid jet to effectively cut the tissue and/or bone.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for cutting tissue, comprising:
   cutting tissue at a target site using a high pressure fluid jet delivered from a nozzle through a liquid environment; and
   heating the liquid environment surrounding the high pressure fluid jet outside of the nozzle to form at least one vapor bubble adjacent to the fluid jet, the vapor bubble reducing friction between the fluid jet and the liquid environment.

2. The method of claim 1, wherein the nozzle includes a heating element formed on an outer surface thereof, and wherein heating the liquid environment comprises delivering energy to the heating element.

3. The method of claim 2, wherein energy delivery is pulsed to form multiple vapor bubbles.

4. The method of claim 2, wherein energy delivery is constant to form a substantially constant vapor bubble.

5. The method of claim 1, wherein the high pressure fluid jet is delivered at a pressure in the range of about 500 psi to 15000 psi.

6. A method for cutting tissue, comprising:
   delivering a high pressure fluid jet from a nozzle having an opening formed in a distal end thereof; and
   activating a heating element disposed on an external surface of a distal end of the nozzle and surrounding the opening formed in the nozzle to heat fluid surrounding the high pressure fluid jet flowing from the nozzle to form at least one vapor bubble that reduces interaction between the high pressure fluid jet and the fluid surrounding the high pressure fluid jet.

* * * * *